United States Patent [19]

DeSimone

[11] 4,219,450

[45] Aug. 26, 1980

[54] PROPENE TRIMER AND TETRAMER OXIMES IN PERFUMES

[75] Inventor: Robert S. DeSimone, Middletown, N.Y.

[73] Assignee: Hercules Incorporated, Wilmington, Del.

[21] Appl. No.: 941,101

[22] Filed: Sep. 8, 1978

[51] Int. Cl.$^2$ ............................ A61K 7/46; C11B 9/00
[52] U.S. Cl. ............................ 252/522 R; 260/566 A; 252/174; 252/174.11; 424/64; 424/69; 424/76; 424/358
[58] Field of Search .................... 252/522; 260/566 A

[56] References Cited

U.S. PATENT DOCUMENTS

| | | | |
|---|---|---|---|
| 3,751,468 | 8/1973 | Olechowski | 260/566 A |
| 4,053,438 | 10/1977 | DeSimone | 252/522 R |

OTHER PUBLICATIONS

Givaudan Brochure: Givaudan Chemical and Specialties "Stemone", Givaudan Corp. Clifton, N.J.

*Primary Examiner*—Veronica O'Keefe
*Attorney, Agent, or Firm*—William S. Alexander

[57] ABSTRACT

Oximes of propene trimers and propene tetramers are disclosed which are new compositions of matter. These oximes are useful as perfume components in, e.g., colognes and perfumes and as fragrances in detergents and cosmetics.

4 Claims, No Drawings

PROPENE TRIMER AND TETRAMER OXIMES IN PERFUMES

The art of perfumery, having its origins in antiquity, has until very recent times relied predominantly on natural perfume essence oils for its pallette. Rapidly expanding population in modern times with concomitant changes in economic patterns and land use have made an unfavorable environment for the cultivation of essential oil crops. This has resulted in an increasingly sporadic, uneconomic, and insufficient supply of natural fragrance oils. As a result, the modern perfumer has devoted much of his time to replacing natural materials with synthesized raw materials which can be produced in both consistent quality and controllable cost from petrochemicals.

An aspect which has presented a problem to the perfumers while using synthetic raw materials is that of duplicating the rounded (blended) and full bodied effect of natural essential oils. These materials are normally quite complex with respect to trace ingredients which more often than not make important contributions to the odor profile, augmenting the odor strength, and blending the odor profile of the constituents. Accordingly, there is a continued search, which is especially evident within the last decade, for materials of unique odor character which can lend novel effects to modern perfumes and provide "lift" and strength enhancement sought with perfumes containing dominant proportions of petrochemically based raw materials.

It is an object of this invention to provide new and useful synthetic chemical compounds derived from inexpensive petrochemical feedstocks. Another object is to provide methods for preparing such perfumery chemicals. Yet another object is to provide perfume compositions containing, as essential ingredients thereof, the novel chemicals of this invention.

The novel chemical compounds of this invention are propene trimer oxime and propene tetramer oxime. These compounds, which can be prepared by known synthetic methods from commercially available propene trimer and tetramer and isolated as complex isomeric mixtures, are found to have very useful floral perfume odor characteristics.

The propene trimer starting material is a complex mixture of branched chain monoolefins containing principally isononenes having the structural formula:

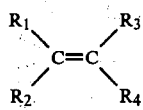

wherein $R_1$, $R_2$, $R_3$ and $R_4$ are hydrogen or aliphatic hydrocarbon radicals having 1 to 7 carbon atoms and the total of carbon atoms among $R_1$, $R_2$, $R_3$ and $R_4$ is 7. The structures for the nonenes contained in the trimer have been described as typically falling within the ranges shown in the following table:

TABLE I

| Isomer Distribution of Commercial Propene Trimer | |
|---|---|
| Olefin Type | % Range |
| $RCH=CH_2$* | 1 to 4 |
| $RCH=CHR$* | 14 to 15 |
| $R_2C=CH_2$ | 8 to 11 |
| $R_2C=CHR$ | 35 to 37 |

TABLE I-continued

| Isomer Distribution of Commercial Propene Trimer | |
|---|---|
| Olefin Type | % Range |
| $R_2C=CR_2$ | 33 to 42 |

*At least one R has a branched chain in these structures.

A typical propene trimer has a refractive index ($N_D^{20}$) within the range from about 1.4230 to about 1.4280, a boiling range from about 135° to about 145° C. and a density within the range from about 0.7350 to about 0.7450. Using a 6'×1/4" stainless steel gas-liquid chromatography (GLC) column packed with Carbowax 20M on Chromasorb W, programmed from 75° C. to 160° C. at 4° C. per minute and 8-minute hold at 160° C., the GLC retention time is about 2.5 to 5.5 minutes. GLC analysis of a commercial propene trimer distinguishes in excess of 90 isomers of the 9-carbon backbone with, very likely, many more unresolved.

The propene tetramer starting material is a complex mixture of 10 to 15 carbon branched chain monoolefins described by one manufacturer (Sun Oil Company) as shown below:

| Component Monoolefin | Per Cent |
|---|---|
| C-9's | 0.0 |
| C-10's | 2.1 |
| C-11's | 15.7 |
| C-12's | 73.1 |
| C-13's | 6.7 |
| C-14's | 1.3 |
| C-15's | 0.2 |

A typical commercially available propene tetramer mixture has and $N_D^{20}$ of 1.4638, a specific gravity of 0.7670 and a GLC profile consisting of an envelope extending between about 9.5 and 18.9 minutes retention time, with maxima of 11.4 and 12.0 minutes when chromatographed at 10° to 220° C. at 4 degrees/minute on a column 6'×1/4", comprised of stainless steel, and packed with 20% Carbowax 20M on Chromasorb W.

The propene trimer oxime mixture of this invention can be derived in a three-step sequence by known synthetic methods from commercial propene trimer. The trimer first is epoxidized with a peracid such as peracetic acid or persulfuric acid. The resulting epoxide is then rearranged to the ketone using an acid catalyst such as an activated clay, a Friedel Crafts catalyst such as stannic chloride, or by a proton acid such as phosphoric acid or potassium bisulfate. The ketone can alternatively be made by performing the expoxidation of the olefin under acid conditions such as would be the case when employing commercial peracetic acid without a neutralizing agent to remove sulfuric acid, which is normally present in peracetic acid as a stabilizer. The ketone is in turn converted to the desired product oxime mixture by reaction with hydroxylamine or one of its salts such as the sulfate or hydrochloride.

The propene tetramer oxime is prepared in an analogous manner.

The product oxime mixture in both the case of the propene trimer oxime and propene tetramer oxime can be characterized by means of its refractive index, its density, its boiling points and boiling range, its gas-liquid chromatogram, and its odor, to give a product for perfumery of reproducible and useful organoleptic quality. In particular, the propene trimer oxime mixture is characterized by its GLC profile when chromatographed on a six-foot by one-quarter inch stainless steel column packed with 20% SE30 on acid-washed Chromasorb W operated at 100° to 220° C., programmed at 4° per minute, with a helium flow of about 60 ml. per minute. More specifically, the propene trimer oxime and the useful fractions thereof can be characterized by:

| | |
|---|---|
| Refractive Index ($N_D^{20}$) Range | 1.4417 to 1.4578 |
| Specific Gravity Range ($D_{20}$) | 0.8735 to 0.8929 |
| Boiling Range | 53 to 70° C. at 1.0 to 0.8 mm. Hg |
| GLC Retention Times (conditions described above) | A peak envelope having a maximum at 14.8 minutes with isomers extending from 10.5 to 18 minutes. |

The propene tetramer oxime mixture is characterized in particular by means of its GLC profile when chromatographed under the same conditions as for the propene trimer oxime noted above. More specifically, the propene tetramer oxime and the useful fractions thereof can be characterized by:

| | |
|---|---|
| Refractive Index ($N_D^{20}$) Range | 1.4595 to 1.4620 |
| Specific Gravity Range ($D_{20}$) | 0.8764 to 0.8841 |
| Boiling Range | 86 to 104° C. at 0.07 to 0.1 mm. Hg |
| GLC Retention Times (conditions described above) | A peak envelope having maxima at 19.7, 21.4 and 22.5 minutes with isomers between 12 and 26 minutes. |

The use of oximes of 9 and more carbon atoms in perfumery has not heretofore been known. To date, the highest carbon number oxime used has been an 8 carbon compound, and its odor is completely different from that of the oximes described herein. It has been described by the manufacturer as having a bitter, green leaf odor suggestive of fig leaves.

The propene trimer oxime mixture of this invention possesses a surprising and unexpectedly cohesive violet note with a green stem background. It odor is also described by perfumers as pyrazinic, with a tobacco leaf effect. It has been found useful in galbanum and herbal fragrance combinations. These well-rounded odor effects are unexpected from such a complex mixture.

The propene tetramer oxime mixture possesses a novel, highly useful and well-rounded green floral herb note. The mixture also has been described by some perfumers as having pyrazinic character and a paprika note. The product has an unexpected blended character which when used in a green herbal odor grouping has been found to provide a chamomile effect. It can be used to support the green effect often sought for modern perfumery accords.

Individual fractions of the mixtures possess their own distinctive odor characteristics. These will be described as various fractions are described in the examples hereinafter.

EXAMPLE I, PROPENE TRIMER OXIME

PROPENE TRIMER OXIME, STEP I

Propene Trimer Epoxide

Into a twelve liter three-necked round bottom flask equipped with mechanical stirrer, side arm addition funnel, condenser and thermometer was charged 900 g. of commercial propene trimer (7.1 M), 155 g. of sodium acetate (1.9 M) and 1500 g. of methylene chloride. A 1488 g. solution of 40% peracetic acid (7.8 M) was added dropwise with cooling over two hours at between 15° and 19° C. Stirring at between 13° and 27° C. was continued for three more hours after the addition was complete. An 1100 g. portion of water was added with agitation, the aqueous phase being separated and discarded. The solution was then washed with 1000 ml. of 10% NaOH solution followed by washing with 1000 ml. of water. The organic phase was dried over sodium sulfate and methylene chloride removed under vacuum at 25 mm Hg. Distillation was performed under the following parameters on a one foot by one inch seven plate Goodloe column:

| Fraction | Weight (g) | Time (hr) | Pot (°C.) | Head (°C.) | Vacuum (mmHg) | Epoxide % GLC |
|---|---|---|---|---|---|---|
| 1 | 33.9 | 0 | 70 | 61 | 25 | 86.2 |
| 2 | 46.5 | 0.58 | 71 | 62 | 25 | 98.2 |
| 3 | 35.5 | 1.08 | 71 | 62 | 25 | 99.4 |
| 4 | 87.8 | 1.55 | 76 | 65 | 25 | 99.8 |
| 5 | 334.5 | 2.80 | 85 | 66 | 25 | 99+ |
| 6 | 317.0 | 5.03 | 108 | 70 | 25 | 99+ |
| 7 | 35.6 | 5.33 | 140 | 70 | 25 | −95 |
| 8 | 14.2 | 5.66 | 215 | 75 | 25 | |

There was thus obtained 905 g. of distillate containing approximately 883 g. of propene trimer epoxide.

PROPENE TRIMER OXIME, STEP II

Propene Trimer Ketone

A three liter flask was equipped with a mechanical stirrer, thermometer and side arm dropping funnel A mixture of 1100 g. of toluene and 150 g. of Tonsil (activated clay) was heated to reflux with stirring (90° C.) and 900 g. of the above prepared propene trimer epoxide was added dropwise at 87° to 93° C. over one and one-half hours. Reflux was continued for two hours after the addition was complete. After cooling, the filtered solution was neutralized to pH 8.0 with 10% NaOH and was washed three times with 300 ml. portions of water. The solution was dried over sodium sulfate and distilled under the following parameters on a one foot by one inch Goodloe column:

| Fraction | Weight (g) | Time (hr) | Pot (°C.) | Head (°C.) | Vacuum (mmHg) |
|---|---|---|---|---|---|
| 1 | 67.5 | 0 | 104 | 45 | 5 |
| 2 | 43.3 | 0.67 | 90 | 41 | 5 |
| 3 | 63.4 | 1.83 | 90 | 42 | 5 |
| 4 | 85.0 | 1.91 | 95 | 43 | 5 |
| 5 | 64.2 | 3.58 | 105 | 50 | 5 |
| 6 | 42.0 | 4.58 | 100 | 52 | 0.9 |
| 7 | 40.0 | 6.08 | 120 | 60 | 0.1 |
| 8 | 58.6 | 7.38 | 145 | 70 | 0.1 |
| 9 | | 9.38 | 175 | 90 | 0.1 |
| 10 | 87.9 | 10.38 | 158 | 90 | 0.1 |
| 11 | 82.2 | 11.38 | 170 | 95 | 0.1 |

Fractions one through six were bulked as product, 364 g.

PROPENE TRIMER OXIME, STEP III

Propene Trimer Oxime

A one liter flask was equipped with a condenser, heating mantle, mechanical stirrer, thermometer and addition funnel. Hydroxylamine hydrochloride, 153 g., was charged into the flask along with 600 ml. ethanol and 88 g. of sodium hydroxide. The mixture was heated to reflux and 285 g. of propene trimer ketone made in the previous step was added dropwise at 80° C. over 30 minutes. Reflux was continued for two hours, the solution cooled and 600 ml. of water added. GLC at this point showed 75% conversion to oxime. The aqueous phase was separated and then back-extracted with 400 ml. of methylene chloride. The combined organics were evaporated on a rotary evaporator to give 310 g. of crude product which was rectified on a one foot by one inch Goodloe column under the following parameters:

| Fraction | Weight (g) | Time (hr.) | Pot (°C.) | Head (°C.) | Vacuum (mm Hg) | % Oxime (GLC) | $D_{20}$ | $N_d^{20}$ |
|---|---|---|---|---|---|---|---|---|
| 1 | 12.8 | 0 | 85 | 36 | 1.0 | | | |
| 2 | 16.5 | 0.42 | 87 | 36 | 1.0 | | 0.8600 | 1.4355 |
| 3 | 8.8 | 1.42 | 97 | 53 | 1.0 | | 0.8735 | 1.4417 |
| 4 | ≅10.0 | 2.09 | 97 | 55 | 0.8 | | 0.8750 | 1.4502 |
| 5 | 17.0 | 2.84 | 98 | 55 | 0.8 | 99.7 | 0.8865 | 1.4545 |
| 6 | 50.3 | 3.84 | 98 | 58 | 0.8 | 99.5 | 0.8900 | 1.4568 |
| 7 | 57.6 | 6.01 | 106 | 62 | 0.8 | 99.5 | 0.8909 | 1.4572 |
| 8 | 24.5 | 6.17 | 106 | 64 | 0.8 | 99.5 | 0.8920 | 1.4578 |
| 9 | 23.7 | 6.42 | 108 | 65 | 0.8 | 99.5 | 0.8929 | 1.457 |
| 10 | 16.4 | 6.45 | 120 | 69 | 0.8 | 99.5 | 0.8927 | 1.4578 |
| 11 | 10.8 | 6.66 | 170 | 70 | 0.8 | 99.5 | 0.8920 | 1.4572 |

Residue = 14 g., contained some product.

The IR spectrum of the oxime showed a strong broad band at 3270 $Cm^{-1}$ (OH stretch vibration), a weak, broad band at about 1655 $Cm^{-1}$ (C=N stretch vibration) and a strong, very broad bank at 938 $Cm^{-1}$ (N—O stretch vibration).

A bulking was made of fractions 6 to 10 for odor evaluation. The product was green-paprika-like (pyrazinic), with tobacco leaf character, buccu-like (minty) and earthy. It was also described by the perfumers as having a violet note with a green stem background. Fragrance notes of individual fractions were described by perfumers as follows:

Fraction 6—Warm, fruity, green
Fraction 7—Leafy, green violet
Fraction 8—Green, fresh persimmon
Fraction 9—Stem-like woody
Fraction 10—Tart-fruity.

EXAMPLE II, PROPENE TETRAMER OXIME
PROPENE TETRAMER OXIME, STEP I
Propene Tetramer Epoxide Into a twelve liter three-necked round bottom flask equipped with a mechanical stirrer, thermometer, condenser and addition funnel was charged 2300 g. of propene tetramer (13.8 M, Sunoco), 444 g. of sodium acetate (5.4 M) and 3200 g. of methylene chloride. Peracetic acid (2731 g., 14.4 M) was then added with cooling at between 15° and 23° C. over 3.5 hours. Stirring was continued at ambient temperature for an additional three hours after the addition was complete. Two liters of water were stirred in and the water separated and discarded. The organic phase was then washed with two more liters of water, 1500 ml. of 10% sodium carbonate solution (to pH 7.9) and then dried over solid anhydrous sodium sulfate.

Distillation was performed on a three foot by one inch 21 plate Goodloe column under the following parameters:

| Time (hr) | Pot Temp. (°C.) | Head Temp. (°C.) | Vacuum (mmHg) | Fraction | Weight (grams) |
|---|---|---|---|---|---|
| 3.75 | 109 | 87 | 10 | 1 | 107 |
| 5.75 | 109 | 81 | 10 | 2 | 205 |
| 8.75 | 120 | 80 | 10 | 3 | 185 |
| 10.00 | 120 | 80 | 10 | 4 | 221 |
| 11.33 | 120 | 83 | 10 | 5 | 231 |
| 11.83 | 120 | 83 | 10 | 6 | 158 |
| 13.83 | 125 | 85 | 10 | 7 | 717 |
| 15.83 | 140 | 90 | 10 | 8 | 253 |
| 16.85 | 150 | 110 | 10 | 9 | 150 |
| 17.66 | 195 | 120 | 10 | 10 | 25 |

Fractions 5 through 8 were bulked for use in the next step.

PROPENE OXIME STEP II
Propene Tetramer Ketone

A five liter three-necked morton flask equipped with a mechanical stirrer, thermometer, addition funnel and heating mantle was charged with 1500 g. of toluene and 150 g. of Tonsil (an activated montmorillonite clay). Propene tetramer epoxide (1360 g., 7.44 M) was added at 94° C. over 1.5 hours and reflux was continued for two hours after the addition was complete. The organic phase was filtered away from the clay and neutralized with 10% NaOH (pH 8). The organic was then washed three times with 450 ml. of water, then washed with 100 ml. of 10% NaOH and dried over solid anhydrous sodium sulfate.

Distillation was performed under the following parameters on a three foot by one inch 21 plate Goodloe column:

| Time (hr) | Pot Temp. (°C.) | Head Temp. (°C.) | Vacuum (mmHg) | Fraction | Weight (grams) |
|---|---|---|---|---|---|
| 2.00 | 113 | 70 | 23 | 1 | 28 |
| 3.50 | 120 | 70 | 8 | 2 | 69 |
| 3.87 | 125 | 73 | 8 | 3 | 28 |
| 4.64 | 125 | 75 | 8 | 4 | 45 |
| 5.27 | 125 | 82 | 8 | 5 | 45 |
| 5.94 | 126 | 84 | 8 | 6 | 44 |
| 7.60 | 132 | 85 | 8 | 7 | 80 |
| 8.10 | 135 | 87 | 8 | 8 | 44 |
| 8.60 | 139 | 90 | 8 | 9 | 215 |
| 9.27 | 157 | 95 | 8 | 10 | 236 |
| 10.77 | 155 | 56 | 0.1 | 11 | 38 |
| 11.90 | 180 | 72 | 0.1 | 12 | 80 |

Fractions 6 through 11 were bulked for use in the next step.

PROPENE TETRAMER OXIME, STEP III

Propene Tetramer Oxime

Into a three liter round bottom flask equipped with a mechanical stirrer, thermometer and addition funnel was charged 1200 ml. of ethanol, 150 g. of sodium hydroxide, 261 g. of hydroxylamine hydrochloride and 630 g. of propene tetramer ketone from Step II. The mixture was held at reflux for 2.5 hours and allowed to stir at room temperature overnight. The mixture was diluted with 600 ml. of water and the aqueous phase discarded. The organic phase was then washed with 300 ml. of saturated brine and then flash distilled at 52° to 112° C. head temperature, 125° to 210° C. pot temperature at 0.1 mmHg. This gave 430 g. of crude oxime which was redistilled under the following parameters on a one foot by one inch seven plate Goodloe column:

| Fraction | Time (hr) | Pot Temp. (°C.) | Head Temp. (°C.) | Vacuum (mm Hg) | Weight (g) | $N_D^{20}$ | Comments |
| --- | --- | --- | --- | --- | --- | --- | --- |
| 1 | 1.20 | 128 | 51 | 0.08 | 7.7 | | RR 20/1 |
| 2 | 1.53 | 125 | 50 | 0.08 | 5.7 | | |
| 3 | 2.53 | 123 | 52 | 0.08 | 16.2 | | |
| 4 | 3.75 | 125 | 51 | 0.08 | 16.5 | | |
| 5 | 4.67 | 127 | 54 | 0.08 | 13.0 | | |
| 6 | 5.83 | 127 | 60 | 0.07 | 13.4 | | 25% oxime by glc |
| 7 | 6.83 | 126 | 70 | 0.07 | 10.8 | | 41% oxime |
| 8 | 7.91 | 135 | 80 | 0.07 | 9.1 | | 71% oxime |
| 9 | 8.91 | 145 | 86 | 0.07 | 9.9 | 1.4595 | 98% oxime $D_{20}$ 0.8764 |
| 10 | 9.66 | 134 | 80 | 0.01 | 6.8 | 1.4605 | 99.5% oxime |
| 11 | 10.66 | 136 | 81 | 0.01 | 11.7 | 1.4605 | |
| 12 | 11.83 | 136 | 80 | 0.01 | 10.8 | 1.4602 | |
| 13 | 13.08 | 142 | 95 | 0.01 | 10.7 | 1.4608 | $D_{20}$ 0.8815 |
| 14 | 14.08 | 143 | 95 | 0.01 | 10.7 | 1.4609 | |
| 15 | 15.00 | 134 | 80 | 0.01 | 15.1 | 1.4605 | |
| 16 | 16.00 | 134 | 82 | 0.01 | 19.1 | 1.4610 | |
| 17 | 17.58 | 134 | 82 | 0.01 | 14.4 | 1.4610 | |
| 18 | 18.60 | 134 | 83 | 0.01 | 12.4 | 1.4610 | $D_{20}$ 0.8826 |
| 19 | 19.63 | 135 | 82 | 0.01 | 19.5 | 1.4610 | |
| 20 | 20.46 | 137 | 86 | 0.01 | 21.8 | 1.4612 | RR 10/1 |
| 21 | 22.21 | 139 | 85 | 0.01 | 17.8 | 1.4618 | |
| 22 | 23.54 | 145 | 85 | 0.01 | 24.5 | 1.4618 | RR 5/1 |
| 23 | 23.67 | 143 | 86 | 0.01 | 24.0 | 1.4618 | $D_{20}$ 0.8812 |
| 24 | 23.95 | 145 | 88 | 0.01 | 20.1 | 1.4620 | RR 2/1 |
| 25 | 24.00 | 132 | 80 | 0.01 | 13.1 | 1.4620 | |
| 26 | 24.48 | 145 | 84 | 0.01 | 20.7 | 1.4620 | |
| 27 | 24.61 | 190 | 104 | 0.01 | 11.8 | 1.4620 | $D_{20}$ 0.8841 |

Fractions 15 through 25 were bulked as useful product. An ammoniacal topnote was removed by washing with 10% phosphoric acid. Fractions 6 through 10 and 27 were saved for recycle.

The IR spectrum of the oxime showed a strong, broad band at 3340 Cm$^{-1}$ (OH stretch vibration), a weak band at about 1658 Cm$^{-1}$ (C=N stretch vibration) and a medium strong, broad band at 942 Cm$^{-1}$ (No stretch vibration).

The product had a burnt green paprika note with a green pyrazinic dry-out. It was also described by the perfumers as having a green floral herb note.

Fragrance notes of individual fractions were described as follows:

Fraction 14—Clean, woody, green violet, fatty
Fraction 16—Clean, woody, green, jasmine
Fraction 18—Clean, woody, green, jasmine
Fraction 20—Clean, woody, green, jasmine
Fraction 22—Clean, woody, jasmine
Fraction 24—Clean, woody, jasmine Fractions 14 through 18, when bulked, gave a fresh, green aroma body. Fractions 20 through 24 form a different complex having a jasmine, woody character.

The propene trimer and tetramer oximes are used in any olfactorily effective amount, but usually in combination with at least one and usually several or many other olfactorily active ingredients to form perfume compositions. In blends with such other ingredients, they can constitute up to about 75%, preferably up to about 50%, and most preferably about 0.5 to 50% by weight of the total perfume composition. They can be used in any perfumery applications as, e.g., colognes, perfumes, and as detergent and cosmetic fragrances. The fresh, floral, herbal note associated with these compounds makes them particularly useful in narciss, hyacinth, lilac and tuberose compositions where the green and herbal notes are important.

EXAMPLE III, GREEN FLORAL FRAGRANCE BASE UTILIZING PROPENE TRIMER OXIME

| Ingredient | Percentage |
| --- | --- |
| Propene Trimer Oxime as per Example 1 | 3.5 |
| 3,7-Dimethyl-1,6-nonadien-3-ol | 6.5 |
| Hexanol-1- | 0.2 |
| Acetaldehyde-cis-3-hexenyl acetal | 1.0 |
| Cis-3-hexenol-1- | 0.2 |
| Isolongifolene epoxide | 20.0 |
| Styralyl acetate | 1.5 |
| Phenyl acetaldehyde dimethyl acetal | 0.2 |
| 2-Nonenal (1% solution in dipropylene glycol) | 1.0 |
| 2-Trans hexenal | 0.1 |
| 2-Trans hexenol | 0.5 |
| Bergamot oil | 6.6 |
| Hydroxy citronellal | 20.0 |
| 2-Trans-6-cis-nonadienal (1% in dipropylene glycol) | 0.2 |
| Terpineol extra | 3.0 |
| Galbanum oil | 1.5 |
| Linalool | 25.0 |
| Methyl ester of hydrogenated rosin acid; | 5.0 |
| 5-Acetyl-1,1,2,3,3,6-hexamethylindan | 1.0 |
| 7-Acetyl-1,1,3,4,4,6-hexamethyl-1,2,3,4-tetrahydronaphthalene | 1.5 |

| Ingredient | Percentage |
|---|---|
| Isopropyl myristate | 2.5 |

EXAMPLE IV, FLORAL HERBAL FRAGRANCE BASE UTILIZING PROPENE TETRAMER OXIME

| Ingredient | Percentage |
|---|---|
| Cis-3-hexenol | 0.5 |
| Ethyl nonanoate | 0.5 |
| Lavender oil | 0.5 |
| Propene tetramer oxime | 5.0 |
| Diethyl malonate | 20.0 |
| Linalool | 400.0 |
| Bergamot oil | 5.0 |
| Rosemary oil | 2.0 |
| Hexyl cinnamic aldehyde | 3.5 |
| Methyl ester of hydrogenated rosin acid | 5.5 |
| Isolongifolene epoxide | 7.0 |
| 2-Heptyl cyclopentanone | 1.0 |
| 2,3,-Dimethy-2-nonenoyl nitrile | 0.5 |
| 2-Hexyl-3-keto cyclopentane carboxylic acid methyl ester | 5.0 |

EXAMPLE V, FRAGRANCE BASE UTILIZING PROPENE TRIMER OXIME

| Ingredient | Percentage |
|---|---|
| Bergamot oil | 22.0 |
| Lemon oil, Sicilian | 6.0 |
| Patchouly oil | 5.0 |
| Ylang ylang | 2.0 |
| Sandalwood oil | 3.0 |
| Benzyl salicylate | 10.0 |
| 2-Hexyl-3-Keto cyclopentane carboxylic acid methyl ester | 10.0 |
| Oakmoss absolute | 0.5 |
| Hydroxy citronellal | 13.5 |
| Styrallyl acetate | 1.0 |
| Gamma methyl ionone | 3.5 |
| Undecylenic aldehyde (10% in diethyl phthalate) | 2.0 |
| Lyral (IFF Trademark) | 3.0 |
| Musk ambrette | 8.0 |
| Propene trimer oxime | 0.5 |

The perfume with the propene trimer oxime had a much fuller, cohesive odor effect than the same mixture not containing the propene trimer oxime of this invention.

EXAMPLE VI, FRAGRANCE BASE UTILIZING PROPENE TETRAMER OXIME

| Ingredient | Percentage |
|---|---|
| Ylang ylang | 3.0 |
| Benzyl acetate | 4.0 |
| Jasmal (IFF Trademark) | 2.5 |
| Linalool | 4.0 |
| Oakmoss absolute | 1.0 |
| Patchouly oil | 2.0 |
| Benzoin resinoid | 2.5 |
| Galbanum oil | 0.5 |
| Lyral (IFF Trademark) | 1.5 |
| 2-Hexyl-3-keto cyclopentane carboxylic acid methyl ester | 12.0 |
| Styralyl acetate | 0.5 |
| Hydroxy citronellal | 10.0 |
| Phenyl ethyl alcohol | 2.5 |
| Piconia (IFF Trademark) | 9.0 |
| Vetiveryl acetate | 4.0 |
| Sandela (Givaudan Trademark) | 6.0 |
| Vertofix Coeur (IFF Trademark) | 8.0 |
| Gamma methyl ionone | 2.5 |
| Undecalactone (10% in diethyl phthalate) | 0.5 |
| Coumarin | 0.5 |
| Cis-3-hexenyl benzoate | 1.0 |
| Cis-3-hexenyl salicylate | 1.0 |
| Phenyl acetaldehyde dimethyl acetal | 0.5 |
| Cis jasmone (10% in diethyl phthalate) | 1.0 |
| Musk ambrette | 1.0 |
| Musk ketone | 1.0 |
| Geraniol | 6.0 |
| Lavender oil | 2.0 |
| Geranium oil | 1.0 |
| Grisambrol (Firmenich Trademark) | 1.0 |
| Propene tetramer oxime | 7.5 |

The above perfume containing the propene tetramer oxime had a much better blended, fuller, and coherent odor effect than the same mixture not containing the same.

What I claim and desire to protect by Letters Patent is:

1. A perfume composition comprising an olfactorily effective amount of a propene trimer oxime or a propene tetramer oxime and at least one other olfactorily active ingredient.

2. A composition according to claim 1 wherein the olfactorily effective amount of the oxime is about 0.5 to 50% by weight.

3. A composition according to claim 1 wherein the oxime is propene trimer oxime.

4. A composition according to claim 1 wherein the oxime is propene tetramer oxime.

* * * * *